US009193677B2

(12) United States Patent
Oster

(10) Patent No.: US 9,193,677 B2
(45) Date of Patent: Nov. 24, 2015

(54) METAL SALTS OF A DIALKYL ESTER OF 5-SULFOISOPHTHALIC ACID AND METHOD OF PREPARING SAME

(75) Inventor: Timothy Oster, Batesville, AR (US)

(73) Assignee: FutureFuel Chemical Company, Clayton, MO (US)

( * ) Notice: Subject to any disclaimer, the term of this patent is extended or adjusted under 35 U.S.C. 154(b) by 0 days.

(21) Appl. No.: 13/409,943

(22) Filed: Mar. 1, 2012

(65) Prior Publication Data

US 2012/0225981 A1     Sep. 6, 2012

Related U.S. Application Data

(60) Provisional application No. 61/460,773, filed on Mar. 2, 2011.

(51) Int. Cl.
| | |
|---|---|
| *C08K 5/42* | (2006.01) |
| *C07C 303/44* | (2006.01) |
| *C07C 309/58* | (2006.01) |
| *C07C 303/22* | (2006.01) |
| *C07C 303/32* | (2006.01) |
| *C08G 69/26* | (2006.01) |
| *C08G 69/42* | (2006.01) |
| *C08K 5/098* | (2006.01) |

(Continued)

(52) U.S. Cl.
CPC ............. *C07C 303/22* (2013.01); *C07C 303/32* (2013.01); *C07C 303/44* (2013.01); *C08G 69/265* (2013.01); *C08G 69/42* (2013.01); *C08K 5/42* (2013.01); *C08K 5/098* (2013.01); *C08L 67/02* (2013.01); *C08L 77/06* (2013.01)

(58) Field of Classification Search
CPC ....... C07C 303/22; C07C 303/32; C08K 5/42
USPC ............................................. 524/158; 560/14
See application file for complete search history.

(56) References Cited

U.S. PATENT DOCUMENTS

| | | | |
|---|---|---|---|
| 3,088,956 A | 5/1963 | Horn et al. | |
| 3,185,671 A | 5/1965 | Horn | |

(Continued)

FOREIGN PATENT DOCUMENTS

| | | |
|---|---|---|
| CN | 1203909 | 1/1999 |
| CN | 1673450 | 9/2005 |

(Continued)

OTHER PUBLICATIONS

Yu, et al., Synthesis of sodium bis(2-hydroxyethyl) 5-sulfoisophthalate, Huaxue Shijie, 2005, pp. 26-29, vol. 46 Issue 1, China.

(Continued)

*Primary Examiner* — John Uselding
(74) *Attorney, Agent, or Firm* — Additon, Higgins & Pendleton, P.A.

(57) ABSTRACT

The claimed invention meets these and other objects by providing a method of preparing a metal salt of a dialkyl ester of 5-sulfoisophthalic acid. Broadly speaking, the method provides for the contacting of a dialkyl ester of 5-sulfoisophthalic acid with a metal cation in a buffered reaction mixture to form the metal salt of the dialkyl ester. The reaction mixture is buffered, at least in part, by the acetate of the metal cation. The method according to invention also encompasses various methods of preparing the dialkyl ester of 5-sulfoisophthalic acid.

10 Claims, 3 Drawing Sheets

(51) Int. Cl.
*C08L 67/02* (2006.01)
*C08L 77/06* (2006.01)

(56) References Cited

U.S. PATENT DOCUMENTS

| | | | |
|---|---|---|---|
| 4,083,893 | A | 4/1978 | Lofquist et al. |
| 4,303,577 | A | 12/1981 | Ridgway et al. |
| 5,348,832 | A | 9/1994 | Sacripante et al. |
| 5,777,164 | A | 7/1998 | Boaz |
| 6,075,115 | A | 6/2000 | Putzig et al. |
| 6,133,382 | A | 10/2000 | Studholme |
| 6,334,877 | B1 | 1/2002 | Studholme |
| 6,355,835 | B1 | 3/2002 | Kulsrestha et al. |
| 6,479,619 | B1 | 11/2002 | Duan |
| 6,703,112 | B1 | 3/2004 | Farooq et al. |
| 6,824,944 | B2 | 11/2004 | Sacripante et al. |
| 6,830,859 | B2 | 12/2004 | Shiraishi et al. |
| 7,943,216 | B2 | 5/2011 | Liu et al. |
| 8,178,648 | B2 | 5/2012 | Torno et al. |
| 8,404,886 | B2 | 3/2013 | Oster |
| 8,772,522 | B2 | 7/2014 | Oster |
| 8,809,565 | B2 | 8/2014 | Oster |
| 8,884,045 | B2 | 11/2014 | Oster et al. |
| 2002/0169273 | A1 | 11/2002 | Duan |
| 2004/0006194 | A1 | 1/2004 | Duan |
| 2004/0242838 | A1 | 12/2004 | Duan |
| 2007/0088133 | A1 | 4/2007 | Heater |
| 2007/0208200 | A1 | 9/2007 | Parker et al. |
| 2007/0270535 | A1 | 11/2007 | Yasui et al. |
| 2009/0054567 | A1 | 2/2009 | Heater |
| 2010/0239512 | A1 | 9/2010 | Morris et al. |
| 2010/0275568 | A1 | 11/2010 | Chikatsune et al. |
| 2010/0298597 | A1 | 11/2010 | Oster |
| 2012/0225981 | A1 | 9/2012 | Oster |
| 2012/0245378 | A1 | 9/2012 | Oster |
| 2014/0323751 | A1 | 10/2014 | Oster |

FOREIGN PATENT DOCUMENTS

| | | |
|---|---|---|
| CN | 200610043229 | 8/2006 |
| CN | 200810097895 | 5/2008 |
| CN | 101279940 | 10/2008 |
| CS | 119642 | 8/1966 |
| CS | 157260 | 12/1973 |
| CS | 157260 | 4/1975 |
| DE | 1938227 | 2/1971 |
| IN | 172789 | 11/1993 |
| IN | WO2009072144 | 6/2009 |
| JP | 48-010043 | 8/1973 |
| JP | 48080539 | 10/1973 |
| JP | 51004142 | 1/1976 |
| JP | 63-275024 | 11/1988 |
| JP | 1992-247064 | 9/1992 |
| JP | 2003-512350 | 4/2001 |
| JP | 2004331527 | 11/2004 |
| JP | 2005145836 | 6/2005 |
| WO | 2005/068554 A1 | 7/2005 |
| WO | 2010128526 A2 | 11/2010 |
| WO | WO2011049940 | 4/2011 |
| WO | 2012/054097 A1 | 4/2012 |
| WO | 2012/118973 A1 | 9/2012 |
| WO | 2013/025784 A1 | 2/2013 |
| WO | 2013/033022 A1 | 3/2013 |

OTHER PUBLICATIONS

Zhao, et. al., Synthesis of medium-temperature SIPE, Hecheng Xianwei Gongye, 2001, p. 5-9, vol. 24 Issue 6, China.
Tang, et. al., Improvement on the synthetic process of dimethyl 5-sulfoisophtalate sodium salt, Qingdao Keji Daxue Xuebao, Ziran Kexueban, 2003, pp. 113-116, vol. 24 Issue 2, China.
Zhang, et. al., New Process for the manufacture of dimethyl 5-sulfoisophtalate sodium salt, Jingxi Huagong, 2000, pp. 633-636, vol. 17 Issue 11, China.
Zhang, Production technique for dimethyl sodiosulfoisophthalate, Juzhi Gongye Bianjibu, 2002, pp. 20-22, vol. 15 Issue 1, China.
Wu, et. al., Study on the production of dyeing modifier SIPM for polyester fiber, Hecheng Xianwei Gongye, 1995, pp. 11-13, vol. 18 Issue 2, China.
Wu, et. al., Synthesis of dyeing improver for cationic dye dyeable polyester fibers, Dalian Ligong Daxue Xuebao, 1995, pp. 434-436, vol. 35 Issue 3, China.
Jiang, Synthesis of sodium 3,5-dimethoxycarbonyl benzene sulfonate, Huagong Shikan, 2000, pp. 21-23, vol. 14 Issue 5, China.
Zhang, et. al., Synthesis of sodium 5-sulfodimethylisophthalate, Jingxi Huagong Bianjibu, 1998, pp. 39-41, vol. 15 Issue 3, China.
Li, et al., Synthesis of sodium dimethyl 5-sulfoisophthalate, Jingxi Huangong Bianjibu, 2003, pp. 50-52, vol. 20 Issue 1, China.
Extended European Search Report for Application No. 12752201.9-1451, Jul. 8, 2014, 7 pages, European Patent Office.
US Statutory Invention Registration H1760 (Elango, Waradaraj et al.) Nov. 3, 1998.
http://www.xuyechem.com/pages/lisipa.htm (Jun. 15, 2008).
International Search Report in counterpart International Application No. PCT/US2012/027288 dated Sep. 24, 2012, pp. 1-2.
Office Action in counterpart European Application No. 12752201.9 dated Jun. 15, 2015, pp. 1-4.
Tian et al., "A New Type of Entanglement Involving Ribbons of Rings and Two Different Kinds of 2D (4,4) Networks (2D+2D+1D) Polycatenated in a 3D Supramolecular Architecture", Crystal Growth and Design, vol. 10, (2010) pp. 3847-3849.
Li et al., "Supramolecular Coordination Complexes with 5-Sulfoisophthalic Acid and 2,5-Bipyridyl-1,3,4-Oxadiazole: Specific Sensitivity to Acidity for Cd(II) Species", Crystal Growth and Design, vol. 10 (2010) pp. 2650-2660.
Liu et al., "Syntheses, Crystal Structures, and Magnetic Properties of Copper(II) and Manganese(II) Compounds Constructed from 5-Sulfoisophthalic Acid (H3SIP) and 2,2'-Bipyridine (bpy) Ligands", Journal of Inorganic Chemistry, (2008) pp. 1157-1163.
Tao et al., "Hydrothermal Syntheses, Crystal Structures and Photoluminenscent Properties of Three Metal-Cluster Based Coordination Polymers Containing Mixed Organic Ligands", Journal of Inorganic Chemistry, (2004) pp. 125-133.
Database CA, Chemical Abstracts Service, Columbus OH, Jaroslav et al., "Monosodium salt of 5-sulfoisophthalic acid". Ki;u 15, 1975, pp. 1-3.
Sun et al., "A novel interpenetrating nickel polymer with mixed ligand containing 1D chain and 2D bilayer motifs constructed by 4,4'-bipy", Inorganic Chemistry Communications, (2004) pp. 683-686.
Kim et al., "A thermally stable nanoporous nickel 5-sulfoisophthalate; crystal structure and adsorption properties", Royal Society of Chemistry, (2004) pp. 2148-2149.
Guo et al., "Synthesis and characterizations of a novel 2-D organic-inorganic hybrid constructed from mixed ligands and mixed-valence copper(I/II)", Inorganic Chemistry Communications, vol. 13, (2010) pp. 262-265.
Lin et al., Poly[u2-4,4'-bipyridine)(u2-3,5-dicarboxybenzenesulfonato)silve(I)], Acta Crystallographica, Section E, Structure Reports, Feb. 6, 2010, pp. m259-m-260.
Lucas, et al., "Substituent dependent dimensionalities in cobalt isophthalate supramolecular complexes and coordination polymers containing dipyridylamine ligands", Inorganica Chimica Acta, (2011) pp. 269-279.
Wu et al., "Synthesis, Structure, and Physical Properties of a Barium Complex with 5-Sulfoisophthalic Acid Sodium Salt", Inorganica Chimica Acta, vol. 378, No. 1, Sep. 2, 2011, pp. 596-601.
Supplementary European Search Report in commonly owned EP Application No. 12824606 dated Feb. 2, 2015, pp. 1-5.
International Search Report in commonly owned International Application No. PCT/US2012/050909 dated Feb. 5, 2013, pp. 1-2.
International Search Report in commonly owned International Application No. PCT/US2012/052526 dated Feb. 21, 2013, pp. 1-2.
Office Action in counterpart Japanese Application No. 2013-556863 dated Sep. 29, 2015, pp. 1-7 [International Pub. WO 2010/128526; U.S. Pat. No. 5,348,832; and JP Pub. No. 2004-331527].

METAL SALTS OF A DIALKYL ESTER OF 5-SULFOISOPHTHALIC ACID AND METHOD OF PREPARING SAME

CROSS REFERENCE TO RELATED APPLICATION

This application claims priority from U.S. Provisional Application No. 61/460,773 filed on Mar. 2, 2011, which is incorporated by reference in its entirety.

BACKGROUND OF THE INVENTION

The present invention pertains to the field of polymer chemistry and specialty chemicals. In particular, the present invention pertains to the field of specialized chemicals that are often associated with dyeing nylon fibers, among other uses. More specifically, the invention pertains to metal salts of a dialkyl ester of 5-sulfoisophthalic acid and methods of preparing them.

The term "nylon" generally encompasses a family of synthetic polymers first developed by DuPont in the 1930's. Since then nylon and nylon fibers have found use in products as diverse as carpet fibers, clothing, sutures, parachutes, and footwear, among other uses.

Nylon fibers, especially those used for carpet fiber, are often classified as to type, depending on the fiber's receptivity to acid dyes and basic or cationic dyes. Cationic dyeable nylon fibers generally exhibit inherent stain resistant properties as compared to other nylon types but traditionally suffered from poorer lightfastness, especially in light shades. This resulted in the under-utilization of cationic dyeable nylon as a carpet fiber.

As expected, considerable time, energy, and resources were devoted to finding new and improved methods to improve the dye absorbing characteristics of cationic dyeable nylon. Over the years, several methods were developed in which very specialized chemicals were added to the basic nylon dyeing process to impart improved cationic dye-ability to the polymer. Metal salts of dialkyl esters of 5-sulfoisophthalic acid are one family of such chemicals. The sodium salt of dimethyl-5-sulfoisophthalic acid (aka: DMSSIPA) is a well known. A few other metal salts are known (such as the lithium salt) and can be used as polymer additives. Research into these salts continues to further refine their polymer modifying characteristics and explore additional uses.

The term "drowning" as used herein means the addition of one liquid component to another liquid component. In other words, the term means pouring a solution or intermediate slurry into a second liquid. As used herein, the term usually refers to the addition of an intermediate solution containing a dialkyl ester of 5-sulfoisophthalic acid to a buffered aqueous solution.

The preparation of any salt of a dialkyl ester of 5-sulfoisophthalic acid typically contains a step in which the dialkyl ester is contacted with a metal cation to form the metal salt.

The contacting step is often accomplished by drowning a solution containing a dialkyl ester of HSIPA into a neutralizing solution buffered by a base such as NaOH, $Na_2CO_3$, $NaHCO_3$, or $Na_2SO_4$ to form the salt product. A further alternative is to add the HSIPA to a single solution containing an alcohol and a base.

The resulting product, the metal salt of a dialkyl ester of 5-sulfoisophthalic acid, is then separated, usually by some filtration method, purified and packaged.

There are several problems associated with these traditional methods of forming metal salts of dialkyl esters of HSIPA. Use of sulfate bases to buffer the drowning step is undesirable because sulfate precipitates on nylon filaments, which leads to filament breakage, decreased product throughput, and inferior product.

In addition, a hazardous byproduct (methyl hydrogen sulfate) is formed in substantial amounts in some processes that utilize high levels of sulfate. Extra equipment and record keeping is required to appropriately handle this hazardous byproduct, which increases production costs.

Similarly, problems exist in those traditional processes that utilize carbonates to buffer the system. The dialkyl ester of HSIPA reacts with the carbonate to produce $CO_2$ gas (a process known as "degassing"), which then generates foam in the product slurry, which in turn complicates materials handling and increases costs. The $CO_2$ may also be subject to regulatory reporting/control, which increases costs.

Accordingly, there is a need for a new method of producing metal salts of the dialkyl ester of HSIPA that avoids the problems associated with current production methods. In particular, there is a need for a manufacturing process that reduces the use of sulfates to reduce or substantially eliminate sulfate related filament breakage. There is also a need for a manufacturing process that reduces the formation of methyl hydrogen sulfate and the regulatory issues associated with it. There is a need for a manufacturing process that reduces or substantially eliminates the costs and problems associated with carbonate based degassing. Finally, there is a need for a method that can serve as a platform to make multiple metal salts of dialkyl esters of 5-sulfoisophthalic acid.

In addition, there is a need for new metal salts of dialkyl esters of 5-sulfoisophthalic acid to expand the portfolio of salts that are available to polymer chemists.

If one looks at the general needs discussed above, it becomes apparent that a common factor related to each is the manner in which the reaction system is buffered. Metal sulfates as the source of metal cations do not provide the necessary buffering and adds undesirable sulfates which can lead to inferior product. Carbonate based buffers lead to degassing, which complicates manufacture. Thus, although there is a general need for a new manufacturing process, a more precise recitation of the industry's need would be: there is a need for a new buffering system for use in making metal salts of dialkyl esters of 5-sulfoisophthalic acid.

The process according to the invention provides a new buffering system and provides a high quality product in a manufacturing process that is efficient from both an engineering and economic perspective. The invention also serves as a platform technology that can be used to make multiple metal salts of dialkyl esters of 5-sulfoisophthalic acid, including several novel salts. Additional benefits of the invention are discussed at the end of the detailed description so that they can be understood in their technical context.

BRIEF SUMMARY OF THE INVENTION

The claimed invention meets these and other objects by providing a method of preparing a metal salt of a dialkyl ester of 5-sulfoisophthalic acid. Broadly speaking, the method provides for the contacting of a dialkyl ester of 5-sulfoisophthalic acid with a metal cation in a buffered reaction mixture to form the metal salt of the dialkyl ester. The reaction mixture is buffered, at least in part, by the acetate of the metal cation. The method according to invention also encompasses various methods of preparing the dialkyl ester of 5-sulfoisophthalic acid.

In a further embodiment, the invention encompasses a composition of matter comprising the reaction product of a metal cation and a dialkyl ester of 5-sulfoisophthalic acid wherein the reaction occurs in a reaction mixture buffered by an acetate of the metal cation.

In a still further embodiment, the invention encompasses novel metal salts of a dialkyl ester of 5-sulfoisophthalic acid.

DETAILED DESCRIPTION

Figure 1:
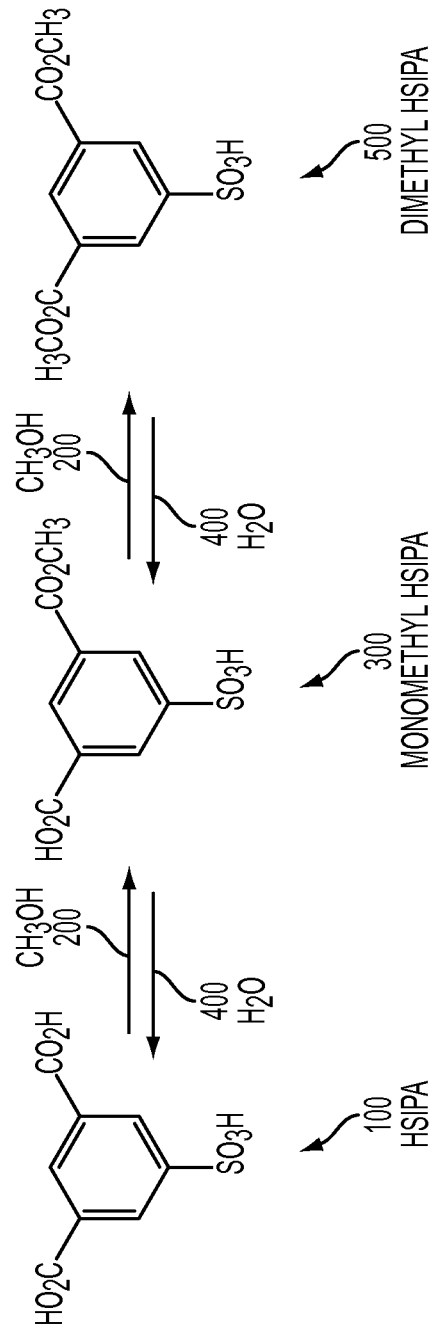
FIG. 1 is a schematic representation of an esterification equilibrium for an exemplary reaction.

In the following description, for purposes of explanation, numerous details are set forth to provide an understanding of one or more embodiments of the present invention. Furthermore, the following detailed description is of the best presently contemplated mode of carrying out the claimed invention based upon existing experimental data. The description is not intended in a limiting sense, and is made solely for the purpose of illustrating the general principles of the invention.

In very broad terms, the invention provides a method of preparing a metal salt of a dialkyl ester of 5-sulfoisophthalic acid. More specifically, the invention provides a method of preparing a metal salt of a dialkyl ester of 5-sulfoisophthalic acid using an improved buffering system that incorporates the acetate of the metal. The method according to the invention also provides very high quality metal salts of a dialkyl ester of 5-sulfoisophthalic acid.

Turning now to the method according to the invention, the invention is a method of preparing a metal salt of a dialkyl ester of 5-sulfoisophthalic acid. The method comprises the step of contacting a dialkyl ester of 5-sulfoisophthalic acid with a metal cation in a buffered reaction mixture to form the metal salt of the metal cation and the dialkyl ester. The buffered reaction mixture is buffered, at least in part, by the acetate of the metal cation. As used herein the terms "metal acetate" and "metal hydroxide" incorporate the metal cation for the desired metal salt.

As noted in the background section and schematically shown in the figures, common commercial methods of making metal salts of dialkyl esters of 5-sulfoisophthalic acid (e.g., DMSSIPA) generally can be broken down into three steps: (1) an esterification step, (2) a neutralization/salt forming step, and (3) a product recovery/purification step. One unique feature of the invention is the use of a metal acetate as a buffer in the neutralization/salt forming step. However, since there are different ways of reaching this step, the following detailed description will begin at a common, early starting point for the manufacture of metal salts of dialkyl esters of 5-sulfoisophthalic acid—the formation of 5-sulfoisophthalic acid and its esterification.

For ease of discussion, the drawings and this detailed description make reference to the manufacture of the sodium salt of dimethyl 5-sulfoisophthalic acid. This narrative aid should not be interpreted to limit the scope of the invention as the invention incorporates many different metal salts as shown by the examples. Furthermore, the examples are not intended to limit the scope of the invention, which is defined by the claims. As will be apparent, those skilled in the art are capable of incorporating the teachings of the invention into a given manufacturing process without undue experimentation.

The process for making metal salts of dialkyl esters of 5-sulfoisophthalic acid can begin with the initial sulfonation of isophthalic acid (IPA) to form 5-sulfoisophthalic acid (HSIPA). In a typical sulfonation reaction isophthalic acid is combined with oleum (aka fuming sulfuric acid) or pure $SO_3$ to form HSIPA. This mixture of sulfuric acid and HSIPA is commonly referred to as a "crude sulfonation mix" and is typically at a low pH due to the presence of sulfuric acid. The HSIPA then undergoes an esterification reaction, typically with an alcohol, to produce an ester of HSIPA.

FIG. 1 is illustrative of an esterification reaction involving HSIPA generally shown by chemical formula 100. Those skilled in the art are aware of the general chemistry utilized in the esterification of HSIPA. Accordingly, only a general outline of the esterification reaction is presented as an aid to the reader.

In the example shown in FIG. 1 methanol ($CH_3OH$) is the alcohol, 200, used in the esterification reaction. The use of methanol in the following paragraphs to illustrate the practice the invention should not be interpreted as limiting the scope of the alcohols that can be used in the practice of the invention. Other straight chain alcohols having from 2 to 6 carbons are also believed to be well suited in the practice of the invention.

Broadly speaking, and as shown in FIG. 1, the esterification reaction can begin by reacting an alcohol, 200, with HSIPA, 100, under conditions sufficient to create an ester linkage with at least one carboxyl group on the HSIPA molecule to form a monoalkyl ester of HSIPA (e.g., monomethyl HSIPA). Water, 400, is a byproduct of this reversible reaction and is preferably removed during the course of the reaction to drive the reaction to the right. Similarly, the resulting monoalkyl ester, 300, reacts with the remaining alcohol to form a dialkyl ester of HSIPA (e.g., dimethyl HSIPA; aka DMHSIPA).

One possible method for conducting the esterification reaction is to combine an alcohol (e.g., methanol) with a crude sulfonation mix under time and temperature conditions sufficient to generate an intermediate sulfonation solution containing a dialkyl ester of 5-sulfoisophthalic acid (e.g., DMHSIPA). This method of conducting the esterification step is known to those skilled in the art and need not be discussed in detail herein. Those skilled in the art are well aware of the time and temperature conditions along with the various reactant ratios (e.g., IPA:oleum; HSIPA:alcohol) that are most efficient for their particular process of forming a dialkyl ester of 5-sulfoisophthalic acid. However, given that the resulting esterification reaction product (i.e., dialkyl-ester) is at a very low pH and contains excessive amounts of sulfates, the product quality obtained with this method is generally poor and the expense required to remove the sulfates and other unwanted side products is economically prohibitive.

Another method of conducting the esterification reaction is to start with isolated HSIPA (e.g., HSIPA that has been removed from a sulfonation mixture) since it is commercially available as a chemical intermediate. In this variation of the method according to the invention, the step of combining or otherwise contacting HSIPA with an alcohol preferably occurs by combining previously isolated HSIPA (which is a solid) with an alcohol (e.g., methanol) in a reaction vessel in a molar ratio of HSIPA:Alcohol of at least 1:2 to form an esterification mixture. In preferred embodiments the HSIPA:Alcohol ratio is between and including 1:2 and 1:10 or higher, more preferably between and including 1:2 and 1:7, and most preferably between and including 1:3 and 1:4. A ratio of 1:3 was found to provide acceptable results in several reactions.

The primary limit on the amount of alcohol used in the process is the cost of the alcohol and the expense/difficulty associated with reclaiming excess alcohol. Methanol is a preferred alcohol. Current data indicates that a molar ratio of HSIPA:alcohol of about 1:3 is sufficient to achieve satisfactory results but this may be adjusted depending on the requirements of a particular manufacturing process.

Regardless of the particular manufacturing process, the esterification phase of the method according to the invention is conducted at temperature conditions sufficient to initiate the esterification reaction to form a dialkyl ester of 5-sulfoisophthalic acid. In preferred embodiments this temperature will range from 20° C. to 111° C. depending on the pressure conditions. In preferred embodiments the temperature range is between 25° C. and 90° C., and more preferably between 30° C. and 80° C. In a particularly preferred embodiment utilizing isolated HSIPA and methanol the esterification phase is conducted in a reaction vessel at the reflux temperature of the reaction mixture, which is usually around 65° C. at atmospheric pressure.

Likewise, the reaction time allowed for the esterification phase of the method can vary substantially based on the temperature and pressure used among other factors. The primary consideration is that the reaction time should be sufficient to achieve a suitable conversion of HSIPA to the dialkyl ester of 5-sulfoisophthalic acid. In preferred embodiments utilizing isolated HSIPA and methanol the reaction time for the esterification phase varies from 10 minutes to 2 hours or longer. The exact combination of time and temperature utilized in any particular practice of the method according to the invention will depend on multiple factors including time constraints, equipment constraints, the chosen alcohol, and energy costs. Those skilled in the art are capable of selecting the operating parameters that are most efficient for their particular manufacturing constraints.

Turning now to the neutralization step/salt formation step of the method according to the invention, the dialkyl ester of 5-sulfoisophthalic acid that is a product of the esterification step is contacted with a metal cation to form the metal salt of the dialkyl ester. The contacting occurs in an aqueous reaction mixture that is buffered, at least in part, by the acetate of the metal cation. The contacting of the dialkyl ester and the metal cation occurs under conditions sufficient to form the metal salt of the metal cation and the dialkyl ester of 5-sulfoisophthalic acid.

In many instances this contact occurs via a "drowning" step. In other words, the solution containing the reaction product of the esterification step (e.g., methanol and the dialkyl ester) is poured into a solution buffered, at least in party, by the metal acetate.

In our illustrative example, the dialkyl ester is dimethyl-5-sulfoisophthalic acid (DMHSIPA) and the metal cation is sodium. (FIG. 2) Continuing with this example, the manner in which the dialkyl ester (DMHSIPA) is contacted with the metal cation (sodium) can vary depending on how the esterification step is conducted. In an exemplary embodiment in which the esterification of HSIPA results in an intermediate sulfonation solution containing a dialkyl ester of HSIPA (i.e., the esterification reaction combined an alcohol such as methanol with a crude sulfonation mixture), the step of contacting the dialkyl ester with a metal cation comprises drowning the intermediate sulfonation solution into a solution buffered by the acetate form of the metal cation.

In the exemplary embodiment in which the esterification step comprises reacting previously isolated HSIPA with an alcohol to form an esterification mixture containing a dialkyl ester of HSIPA, the step of contacting comprises drowning the esterification mixture into a drowning solution buffered by the metal acetate to form a buffered reaction mixture.

Figure 2:
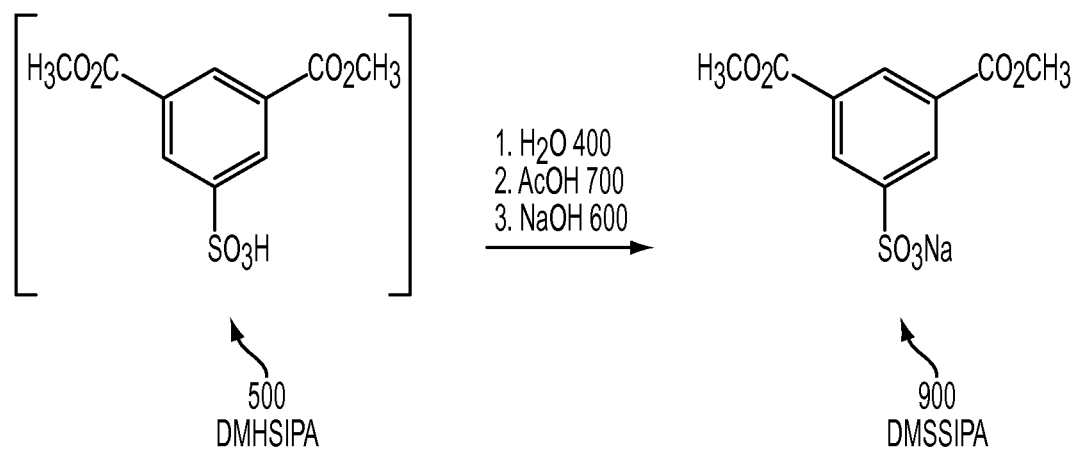
FIG. 2 is a schematic representation of a proposed exemplary reaction process according to the invention.

Each of the above contacting steps generates a reaction mixture containing the desired metal salt of a dialkyl ester of 5-sulfoisophthalic acid (e.g., DMSSIPA) as schematically shown in FIG. 2. In each of the contacting steps the drowning solution is buffered by a quantity of metal acetate sufficient to maintain the pH of the resulting reaction mixture between about 3 to 9. Other buffering agents may also be present in the reaction mixture provided they do not cause unwanted side reactions that interfere with the desired reaction or otherwise lower product quality.

In any of the above described embodiments the aqueous solution and/or resulting reaction mixture buffered by metal acetate may be formed in at least two ways. One approach to forming the buffered solution of metal acetate is to add bulk metal acetate (either anhydrous or in concentrated solution) directly to water.

Alternatively, the solution of metal acetate may be generated in situ by the combination of acetic acid and aqueous metal hydroxide. For example, the esterification mixture from the esterification step that contains the dialkyl ester can be drowned into a reaction vessel containing water and into which acetic acid and a metal hydroxide are separately pumped.

A third option is to use both direct addition of the metal acetate and in situ generation of the metal acetate to provide the metal acetate in solution. In other words, the aqueous solution and the resulting reaction mixture buffered by the metal acetate are formed at least in part by in situ generation or bulk addition of the metal acetate or both.

Although the concentrations of acetic acid and metal hydroxide used in the in situ variation of the invention are not critical to the practice of the invention (for example the concentration of aqueous NaOH can range from 1 to 100%), if aqueous acetic acid and aqueous metal hydroxide are used to generate the solution of metal acetate, the acetic acid should be maintained in molar excess with respect to the metal hydroxide. Excess metal hydroxide can readily raise the pH and induce ester hydrolysis which should be avoided. The exact level of acetic acid molar excess can vary from very little (e.g., 0.01%) to very great (e.g., 30% or more) with the ultimate determination being based on process performance, quality of product, and cost of acetic acid. In preferred embodiments the molar excess of acetic acid is between 1% to 15%. In particularly preferred embodiments the molar excess of acetic acid is between 3% and 10%. During testing the molar excess of acetic acid to aqueous metal hydroxide was kept at or above 4.8%.

Another variable to consider is the ratio of metal hydroxide to the dialkyl ester of HSIPA (MtOH:Di-ester of HSIPA) in those processes that generate the metal acetate in situ. Although the metal hydroxide should be kept deficient with respect to acetic acid in such processes, data indicates that the reaction works best if the metal hydroxide is in molar excess with respect to the initial molar quantity of HSIPA (assuming that most, if not all of the HSIPA reacts to form the dialkyl ester according to the equilibrium of FIG. 1). A molar deficit of the metal hydroxide with respect to HSIPA can result in a molar deficit of the metal cation with respect to the dialkyl ester of HSIPA. Un-reacted dialkyl ester of HSIPA results in lower yields and high residual strong acid values which may lead to low pH and hydrolysis of product. (Note: hydrolysis of the dialkyl ester may occur if the pH is too high or too low.) In most instances it was found that maintaining a molar excess of metal hydroxide between about 0 and 10%, more preferably between 0.5 and 5%, with respect to HSIPA (or the dialkyl ester of HSIPA assuming complete reaction of HSIPA) provided satisfactory results. The same concept of molar excess of metal hydroxide applies in the variation of the method that utilizes the isolated dialkyl ester of HSIPA as a starting material.

In addition, the operational parameters of the contacting step can vary. For example, the temperature of the contacting step is any temperature that is sufficient to generate a metal salt of a dialkyl ester of 5-sulfoisophthalic acid (e.g., DMS-SIPA). The actual temperature utilized can vary depending on time, pressure, components, and energy constraints but normally varies between about 0° C. to about 85° C. In preferred embodiments utilizing methanol as the alcohol the temperature for the contacting step is between about 25° C. to about 85° C., more preferably between about 45° C. to about 80° C.

Similarly, the time and/or rate utilized for contacting the dialkyl ester of 5-sulfoisophthalic acid with the metal cation in the metal acetate buffered solution can vary. The contacting step can be accomplished as rapidly as possible (e.g., 1 to 10 minutes depending on equipment) or it can be extended over several hours. One factor in determining the rate of the contacting step in commercial applications is the ability of practitioner to monitor the pH during the contacting step and adjust the quantity of metal acetate to maintain the appropriate buffering while the dialkyl ester is being added. Again, those skilled in the art are capable of selecting the optimal contacting time for their particular process.

The contacting step (either by drowning or direct addition of isolated dialkyl ester) generates an aqueous reaction mixture comprising a metal salt of a dialkyl ester of 5-sulfoisophthalic acid. It is important to note that the metal cations which lead to the production of the metal salt product may come from the metal acetate or other metal cation source. For example, it is possible to use a combination of bulk metal hydroxide and bulk metal acetate as sources for the metal cation provided appropriate pH parameters are maintained.

In such circumstances one must remain mindful of the molar quantities of the various reactants to aid in calculating the pH of the reaction mixture. However, it is envisioned that in most instances the contacting step will be conducted in a manner that allows for the automated monitoring of the pH and the automated control of the pH via the pumping of aqueous acetic acid and metal hydroxide directly into the reaction vessel.

The remainder of the method according to the invention relates to recovery of the salt product from the reaction mixture.

The desired salt can be recovered/separated from the reaction mixture by cooling the reaction mixture to a temperature sufficient to induce crystallization of the metal salt of the dialkyl ester of 5-sulfoisophthalic acid (e.g., DMSSIPA). The crystallized salt is then separated from the liquid portion of the reaction mixture using known means such as filtration (e.g., nutsche, centrifuge, auto-filter dryer, etc.) to form a cake.

Alternatively, the reaction mixture can be heated to a temperature sufficient to dissolve substantially all of the solids that may be found in the reaction mixture after the reaction takes place. The reaction mixture is then cooled to induce crystallization followed by product separation. During development of the invention it was discovered that heating the reaction mixture dissolve any solids that might be present followed by cooling to induce crystallization improved the quality and filterability of the product. In general, heating the reaction mixture to between 65° C. and 100° C. should be sufficient to dissolve solids in most reaction mixtures. Crystallization normally occurs by the time the reaction mixture is cooled 25° C.

The cake of product can then be washed if desired using any suitable solvent such as water, acetic acid, methanol/water, etc. The product is subsequently dried (i.e., double-cone rotary dryer, spray dryer, vacuum oven, tray dryer, horizontal continuous dryer, etc.) then stored or packaged. Samples produced during development were dried in a vacuum oven at 120° C. to 125° C.

Once the metal salt product is placed into a commercial form it can be added to any number of products where it may add desired properties to those products. The scope of products and potential uses for the metal salts generated in accordance with the invention continues to evolve. However, it is known that some metal salts made in accordance with the invention (e.g., sodium salts) already have uses in some products such as polymers. As used herein the term polymer also includes compositions that are generally known in the industry as "pre-polymers" which are, generally speaking, intermediate polymer compositions capable of further polymerization. Accordingly, the scope of the invention also includes the steps of combining the metal salts with other products, particularly polymers.

As mentioned previously, the method according to the invention provides many improvements over known methods of producing metal salts of dialkyl esters of 5-sulfoisophthalic acid. For example, the method does not use carbonate salts in a drowning step or in the reaction mixture and the lack of degassing allows for a substantially faster transfer of product and a shorter cycle time since there is no concern of the batch 'foaming out' of the reactor. In addition, regulatory reporting of $CO_2$ generation is not needed.

The lack of residual carbonates also improves the quality of the product and reduces unwanted downstream problems such as foaming and products contaminated with carbonates. Similarly, the reduction or elimination of residual sulfates improves downstream processes, particularly nylon processes.

Another benefit of the present invention is that the metal acetate that is present allows the reaction mixture to remain buffered throughout the product separation phase of the process. Keeping the process buffered in a pH range from around 3 to about 9 is known to be important to avoid hydrolysis of ester groups and the subsequent loss of assay. If possible, it is preferable to keep the process buffered between a pH of 3.5 and 4.5. The primary goal is to keep the process buffered so as to avoid hydrolysis.

Furthermore, the acetate anion is commonly used in both nylon and polyester processes as a base to neutralize residual strong acids and/or used as a catalyst. Therefore the presence of residual acetate in the metal salt product should not add a new and complicating component to these polymer processes.

In addition, acetic acid and aqueous metal hydroxide are both liquids and can be directly pumped into a reaction unit (manually or automatically). This is an important improvement over known methods that use solid carbonates. Use of carbonate requires opening the reactor for manual addition of bulk carbonate which exposes workers to methanol vapors. Thus, the use of acetic acid and aqueous metal hydroxide reduces the labor required (the additions can be automated), improves worker safety, and reduces the costs (e.g., certain personal protective equipment is no longer needed).

The method according to the invention has been shown to consistently provide metal salts of dialkyl esters of 5-sulfoisophthalic acid that meet or exceed industry quality requirements.

The method according to the invention has been demonstrated to be quite robust with respect the range of metal salts that can be generated. The method has successfully generated metal salts using metal cations from Groups IA, IIA, VIIA, VIIIA, IB, and IIB of the Periodic Table. Particularly preferred metal cations include sodium, potassium, lithium, rubidium, cesium, magnesium, calcium, strontium, barium, manganese, iron (II), cobalt, nickel, copper (II), zinc, silver (I), and cadmium.

Another aspect of the invention is a composition of matter comprising a metal salt formed by the method according to the invention.

Another aspect of the invention is a composition of matter comprising the reaction product of a metal cation and a dialkyl ester of 5-sulfoisophthalic acid wherein the reaction occurs in a reaction mixture buffered, at least in part, by an acetate of the metal cation. The inventive and claimed compositions of matter are therefore an improvement over other compositions of matter comprising metal salts of a dialkyl ester of 5-sulfoisophthalic acid because the claimed compositions of matter avoid or reduce the presence of carbonates and/or sulfates which can cause manufacturing problems as previously discussed.

The inventive reaction product composition of matter is formed by a process comprising the steps of contacting a dialkyl ester of 5-sulfoisophthalic acid with a metal cation in a reaction mixture buffered, at least in part, by the metal acetate. The process components, parameters, variables, and methods utilized in this embodiment of the invention are the same as those discussed above in relation to the various options for practicing the method according to the invention.

The compositions of matter according to the invention include metal salts comprising metal cations from Groups IA, IIA, VIIA, VIIIA, IB, and IIB of the Periodic Table. Particularly preferred metals cations include sodium, potassium, lithium, rubidium, cesium, magnesium, calcium, strontium, barium, manganese, iron (II), cobalt, nickel, copper (II), zinc, silver (I), and cadmium.

The scope of the invention also encompasses downstream products that incorporate the inventive compositions of matter such as polymers, among other products.

A still another aspect of the invention is the production of novel metal salts of a dialkyl ester of 5-sulfoisophthalic acid. In particular, the invention, as demonstrated in the examples below, has produced several novel metal salts including the cesium, iron (II), cobalt, copper (II), and cadmium salts of 5-sulfoisophthalic acid. In addition, the scope of the invention also encompasses downstream products that incorporate the inventive metal salts such as polymers, among other products.

EXAMPLES

Figure 3:
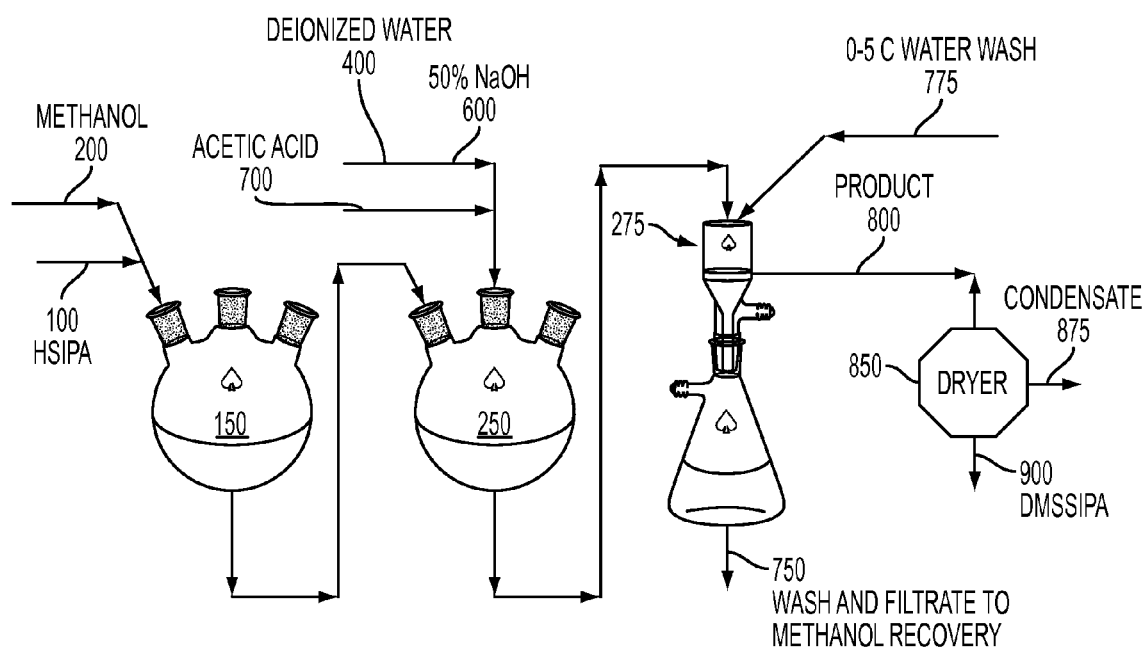
FIG. 3 is a flow chart illustrating one embodiment of the method according to the invention.

The flow chart schematically shown in FIG. 3 outlines the steps utilized in forming metal salts of a dialkyl ester of 5-sulfoisophthalic acid (specifically the sodium salt of dimethyl 5-sulfoisophthalic acid) utilizing a process incorporating in situ generation of metal acetate via the combination of a metal hydroxide and acetic acid. This flow chart is to aid in the understanding of some of the examples and should not be taken as the only method of making a metal salts according to the invention. All of the following examples illustrate the invention through the production of a metal salt of the dimethyl ester of 5-sulfoisophthalic acid.

Example 1

Previously isolated 5-sulfoisophthalic acid (HSIPA) having the following analysis was used in this example: Total Acidity (NaOH in water)=98.2%; Water, % Karl Fisher in pyridine=0.18%; Sulfuric Acid, %=0.16%; APHA Color=71; Iron=1.25 ppm.

Into a 1000 mL round bottom flask (150) add 250 g of methanol (200) and 123 g (dry basis) of HSIPA (100). This mixture was heated to reflux (65° C.) and held at reflux for one hour. The mixture was then cooled to 20° C.-30° C.

Into a separate 2000 mL round bottom flask (250) add 300 g of de-ionized water (400), 33 g of glacial acetic acid (700), and 42 g of sodium hydroxide (50% aqueous) (600). Heat this solution to 45° C.-70° C.

Drown the solution from the 1000 mL flask (150) into the second flask (250) over 1 to 10 minutes.

Warm the resulting product slurry to 75° C.

Cool the product slurry to achieve crystallization of product (about 25° C.).

Filter the product slurry on a sintered glass funnel (275) with a vacuum and wash with water at 0-5° C. if desired (775). The wash and filtrate (750) can go to methanol recovery if desired. Dry the product (800) overnight in a vacuum oven (850) at 125° C. to form a condensate (875) and a final product (900) comprising the sodium salt of dimethyl 5-sulfoisophthalic acid.

The product analyzed as follows:

| Sample 1 - Sodium Salt | |
| --- | --- |
| Product Wet Weight (grams) | 263.1 |
| Product Dry Weight (grams) | 130.3 |
| Solids, % | 49.5 |
| DMSSIPA, Area % LC | 98.31 |
| Sulfate ppm as $SO_4^{2-}$ (IC) | 171 |
| Acidity, % as sulfuric acid | 0 |
| Acetate, ppm as $AcO^{1-}$ (IC) | 2781 |
| Percent Yield (assay basis) | 86.6 |

Example 2

To a 1000 mL round-bottom flask is added 109 g of de-ionized water, 21.9 g of glacial acetic acid and 15.3 g of lithium hydroxide monohydrate. The temperature of the solution is adjusted to 70° C. Slowly, 170 g of DMHSIPA solution (56.15% DMHSIPA in methanol) at ambient temperature is drown into the aqueous solution. The solution is heated to about 79° C. and 44 g of low boilers are removed using vacuum. The solution is cooled to 25° C. and a portion of the solvent allowed to air evaporate to induce crystallization. The product slurry is filtered on a sintered glass funnel with vacuum and dried overnight in a 90° to 100° C. oven. The product analyzed as follows:

| Sample 2 - Lithium Salt | |
| --- | --- |
| Weight, grams | 72.4 |
| DMSIPA, Area % LC | 98.8 |
| Monomethyl SIPA, Area % LC | 1.1 |
| Water, % KF | 0.10 |
| Sulfate, ppm as $SO_4^{2-}$, IC | <100 |
| Acetate, ppm as $AcO^{1-}$, IC | 2777 |

-continued

| Sample 2 - Lithium Salt | |
| --- | --- |
| Strong acid, % as $H_2SO_4$ | 0 |
| Li, x-ray fluorescence | Confirmed |
| Yield, % dry weight | 71.6 |

Example 3

To a 1000 mL round-bottom flask is added 209 g of de-ionized water, 21.9 g of glacial acetic acid and 75.0 g of rubidium hydroxide (50% in water). The temperature of the solution is adjusted to 70° C. Slowly, 170 g of DMHSIPA solution (56.15% DMHSIPA in methanol) is drown into the aqueous solution. The resulting slurry is heated to 77° C., held for 10 minutes and cooled to 25° C. The product slurry is filtered on a sintered glass funnel with vacuum, washed with 40 g of DI-water (0 to 5° C.) and dried overnight in a 90° to 100° C. oven. The product analyzed as follows:

| Sample 3 - Rubidium Salt | |
| --- | --- |
| Weight, grams | 110.2 |
| DMSIPA, Area % LC | 98.6 |
| Monomethyl SIPA, Area % LC | 1.4 |
| Water, % KF | 0.07 |
| Sulfate, ppm as $SO_4^{2-}$, IC | <100 |
| Acetate, ppm as $AcO^{1-}$, IC | 185 |
| Strong acid, % as $H_2SO_4$ | na |
| Rb, x-ray fluorescence | Confirmed |
| Yield, % dry weight | 88.2 |

Example 4

To a 1000 mL round-bottom flask is added 209 g of de-ionized water, 21.9 g of glacial acetic acid and 61.4 g of cesium hydroxide monohydrate. The temperature of the solution is adjusted to 70° C. Slowly, 170 g of DMHSIPA solution (56.15% DMHSIPA in methanol) is drown into the aqueous solution. The solution is held for 10 minutes at 70° C. and cooled to 25° C. The product slurry is filtered on a sintered glass funnel with vacuum, washed with 40 g of DI-water (0 to 5° C.) and dried overnight in a 90° to 100° C. oven. The product analyzed as follows

| Example 4 - Cesium Salt | |
| --- | --- |
| Weight, grams | 95.2 |
| DMSIPA, Area % LC | 99.4 |
| Monomethyl SIPA, Area % LC | 0.6 |
| Water, % KF | 0.06 |
| Sulfate, ppm as $SO_4^{2-}$, IC | <100 |
| Acetate, ppm as $AcO^{1-}$, IC | <100 |
| Strong acid, % as $H_2SO_4$ | na |
| Cs, x-ray fluorescence | Confirmed |
| Yield, % dry weight | 67.3 |

Example 5

To a 1000 mL round-bottom flask is added 105 g of de-ionized water and 19.6 g of magnesium acetate tetrahydrate. The temperature of the solution is adjusted to 23° C. Slowly, 85 g of DMHSIPA solution (56.15% DMHSIPA in methanol) at ambient temperature is drown into the aqueous solution while heating the resulting mixture to 45° C. The slurry is heated to 77° C., held for 5 minutes and cooled to 25° C. The product slurry is filtered on a sintered glass funnel with vacuum, washed with 20 g of DI-water (0 to 5° C.) and dried overnight in a 90° to 100° C. oven. The product analyzed as follows:

| Sample 5 - Magnesium Salt | |
| --- | --- |
| Weight, grams | 42.5 |
| DMSIPA, Area % LC | 98.2 |
| Monomethyl SIPA, Area % LC | 1.8 |
| Water, % KF | 2.39 |
| Sulfate, ppm as $SO_4^{2-}$, IC | 333 |
| Acetate, ppm as $AcO^{1-}$, IC | 1933 |
| Strong acid, % as $H_2SO_4$ | 0 |
| Mg, x-ray fluorescence | Confirmed |
| Yield, % dry weight | 83.5 |

Example 6

To a 1000 mL round-bottom flask is added 105 g of de-ionized water and 16.1 g of calcium acetate hydrate. The temperature of the solution is adjusted to 40° C. Slowly, 85 g of DMHSIPA solution (56.15% DMHSIPA in methanol) at ambient temperature is drown into the aqueous solution. The resulting slurry is heated to 77° C., held for 10 minutes and cooled to 25° C. The product slurry is filtered on a sintered glass funnel with vacuum, washed with 20 g of DI-water (0 to 5° C.) and dried overnight in a 90° to 100° C. oven. The product analyzed as follows:

| Example 6 - Calcium Salt | |
| --- | --- |
| Weight, grams | 41.9 |
| DMSIPA, Area % LC | 99.2 |
| Monomethyl SIPA, Area % LC | 0.8 |
| Water, % KF | 1.4 |
| Sulfate, ppm as $SO_4^{2-}$, IC | <100 |
| Acetate, ppm as $AcO^{1-}$, IC | 397 |
| Strong acid, % as $H_2SO_4$ | 0 |
| Ca, x-ray fluorescence | Confirmed |
| Yield, % dry weight | 81.0 |

Example 7

To a 1000 mL round-bottom flask is added 105 g of de-ionized water, 11.0 g of glacial acetic acid and 24.3 g of strontium(2+) hydroxide octahydrate. The temperature of the solution is adjusted to 28.5° C. Slowly, 85 g of DMHSIPA solution (56.15% DMHSIPA in methanol) is drown into the aqueous solution. The resulting slurry is heated to 77° C. (remained a thick slurry therefore an additional 100 g of de-ionized water was added to thin the slurry), held for 10 minutes and cooled to 25° C. The product slurry is filtered on a sintered glass funnel with vacuum, washed with 30 g of DI-water (0 to 5° C.) and dried overnight in a 90° to 100° C. oven. The product analyzed as follows:

| Sample 7 - Strontium Salt | |
| --- | --- |
| Weight, grams | 47.4 |
| DMSIPA, Area % LC | 97.8 |
| Monomethyl SIPA, Area % LC | 2.2 |
| Water, % KF | 1.4 |
| Sulfate, ppm as $SO_4^{2-}$, IC | 151 |
| Acetate, ppm as $AcO^{1-}$, IC | 1269 |

-continued

| Sample 7 - Strontium Salt | |
|---|---|
| Strong acid, % as $H_2SO_4$ | 0 |
| Sr, x-ray fluorescence | Confirmed |
| Yield, % dry weight | 84.7 |

Example 8

To a 1000 mL round-bottom flask is added 105 g of de-ionized water and 24.3 g of barium acetate. Slowly, 85 g of DMHSIPA solution (56.15% DMHSIPA in methanol) is drown into the aqueous solution while heating to 77° C. An additional 100 g of de-ionized water was added to thin the resulting slurry. The slurry is held for 10 minutes at 77° C., then cooled to 22° C. The product slurry is filtered on a sintered glass funnel with vacuum, washed with 40 g of DI-water (0 to 5° C.) and dried overnight in a 90° to 100° C. oven. The product analyzed as follows:

| Sample 8 - Barium Salt | |
|---|---|
| Weight, grams | 52.5 |
| DMSIPA, Area % LC | 98.7 |
| Monomethyl SIPA, Area % LC | 1.3 |
| Water, % KF | 1.72 |
| Sulfate, ppm as $SO_4^{2-}$, IC | <100 |
| Acetate, ppm as $AcO^{1-}$, IC | 1020 |
| Strong acid, % as $H_2SO_4$ | 0 |
| Ba, x-ray fluorescence | Confirmed |
| Yield, % dry weight | 86.7 |

Example 9

To a 1000 mL round-bottom flask is added 209 g of de-ionized water and 44.8 g of manganese(2+) acetate tetrahydrate. The temperature of the solution is adjusted to 70° C. Slowly, 170 g of DMHSIPA solution (56.15% DMHSIPA in methanol) is drown into the aqueous solution. The solution is cooled to 25° C. The product slurry is filtered on a sintered glass funnel with vacuum, washed with 40 g of DI-water (0 to 5° C.) and dried overnight in a 90° to 100° C. oven. The product analyzed as follows:

| Sample 9 - Manganese Salt | |
|---|---|
| Weight, grams | 92.2 |
| DMSIPA, Area % LC | 98.9 |
| Monomethyl SIPA, Area % LC | 1.0 |
| Water, % KF | 7.47 |
| Sulfate, ppm as $SO_4^{2-}$, IC | <100 |
| Acetate, ppm as $AcO^{1-}$, IC | 304 |
| Strong acid, % as $H_2SO_4$ | na |
| Mn, x-ray fluorescence | Confirmed |
| Yield, % dry weight | 81.5 |

Example 10

To a 1000 mL round-bottom flask is added 94 g of de-ionized water and 9.7 g of iron(2+) acetate. Slowly, 52 g of DMHSIPA solution (56.15% DMHSIPA in methanol) is drown into the aqueous solution while heating the resulting slurry to 70° C. The slurry is held at 70° C. for 5 minutes and cooled to 25° C. The product slurry is filtered on a sintered glass funnel with vacuum, washed with 30 g of DI-water (0 to 5° C.) and dried overnight in a 90° to 100° C. oven. The product analyzed as follows:

| Sample 10 - Iron (II) Salt | |
|---|---|
| Weight, grams | 28.2 |
| DMSIPA, Area % LC | 99.1 |
| Monomethyl SIPA, Area % LC | 0.9 |
| Water, % KF | 5.58 |
| Sulfate, ppm as $SO_4^{2-}$, IC | <100 |
| Acetate, ppm as $AcO^{1-}$, IC | 798 |
| Strong acid, % as $H_2SO_4$ | 0 |
| Fe, x-ray fluorescence | Confirmed |
| Yield, % dry weight | 82.9 |

Example 11

To a 1000 mL round-bottom flask is added 209 g of de-ionized water and 45.6 g of cobalt(2+) acetate tetrahydrate. The temperature of the solution is adjusted to 70° C. Slowly, 170 g of DMHSIPA solution (56.15% DMHSIPA in methanol) is drown into the aqueous solution. The resulting slurry is heated to 78° C. to dissolve solids, held for 10 minutes and cooled to 25° C. The product slurry is filtered on a sintered glass funnel with vacuum, washed with 40 g of DI-water (0 to 5° C.) and dried overnight in a 90° to 100° C. oven. The product analyzed as follows:

| Sample 11 - Cobalt (II) Salt | |
|---|---|
| Weight, grams | 100.2 |
| DMSIPA, Area % LC | 99.2 |
| Monomethyl SIPA, Area % LC | 0.8 |
| Water, % KF | 8.55 |
| Sulfate, ppm as $SO_4^{2-}$, IC | <100 |
| Acetate, ppm as $AcO^{1-}$, IC | 241 |
| Strong acid, % as $H_2SO_4$ | na |
| Co, x-ray fluorescence | Confirmed |
| Yield, % dry weight | 86.9 |

Example 12

To a 1000 mL round-bottom flask is added 105 g of de-ionized water and 22.8 g of nickel(2+) acetate tetrahydrate. The temperature of the solution is adjusted to 24° C. Slowly, 85 g of DMHSIPA solution (56.15% DMHSIPA in methanol) is drown into the aqueous solution while heating the resulting mixture to 73° C. The solution is held for 5 minutes at 73° C., then cooled to 25° C. The product slurry is filtered on a sintered glass funnel with vacuum, washed with 30 g of DI-water (0 to 5 C) and dried overnight in a 90 to 100 C oven. The product analyzed as follows:

| Sample 12 - Nickel (II) Salt | |
|---|---|
| Weight, grams | 46.0 |
| DMSIPA, Area % LC | 99.0 |
| Monomethyl SIPA, Area % LC | 1.0 |
| Water, % KF | 6.35 |
| Sulfate, ppm as $SO_4^{2-}$, IC | <100 |
| Acetate, ppm as $AcO^{1-}$, IC | 1071 |
| Strong acid, % as $H_2SO_4$ | 0 |
| Ni, x-ray fluorescence | Confirmed |
| Yield, % dry weight | 87.3 |

Example 13

To a 1000 mL round-bottom flask is added 209 g of de-ionized water and 36.5 g of copper(2+) acetate hydrate. The temperature of the solution is adjusted to 70° C. Slowly, 170 g of DMHSIPA solution (56.15% DMHSIPA in methanol) is drown into the aqueous solution. The resulting slurry is heated to 77° C., filtered hot to remove insoluble copper compounds, then cooled to 25° C. The product slurry is filtered on a sintered glass funnel with vacuum, washed with 40 g of DI-water (0 to 5° C.) and dried overnight in a 90° to 100° C. oven. The product analyzed as follows:

| Sample 13 - Copper (II) Salt | |
| --- | --- |
| Weight, grams | 68.5 |
| DMSIPA, Area % LC | 99.0 |
| Monomethyl SIPA, Area % LC | 0.9 |
| Water, % KF | 0.66 |
| Sulfate, ppm as $SO_4^{2-}$, IC | <100 |
| Acetate, ppm as $AcO^{1-}$, IC | 145 |
| Strong acid, % as $H_2SO_4$ | 0.4 |
| Cu, x-ray fluorescence | Confirmed |
| Yield, % dry weight | 64.1 |

Example 14

To a 1000 mL round-bottom flask is added 209 g of de-ionized water and 40.1 g of zinc(2+) acetate dihydrate. The temperature of the solution is adjusted to 70° C. Slowly, 170 g of DMHSIPA solution (56.15% DMHSIPA in methanol) is drown into the aqueous solution. The solution is held for 10 minutes at 70° C. and cooled to 25° C. The product slurry is filtered on a sintered glass funnel with vacuum, washed with 40 g of DI-water (0 to 5° C.) and dried overnight in a 90° to 100° C. oven. The product analyzed as follows:

| Sample 14 - Zinc (II) Salt | |
| --- | --- |
| Weight, grams | 96.0 |
| DMSIPA, Area % LC | 99.3 |
| Monomethyl SIPA, Area % LC | 0.7 |
| Water, % KF | 7.12 |
| Sulfate, ppm as $SO_4^{2-}$, IC | <100 |
| Acetate, ppm as $AcO^{1-}$, IC | 207 |
| Strong acid, % as $H_2SO_4$ | 0 |
| Zn, x-ray fluorescence | Confirmed |
| Yield, % dry weight | 83.7 |

Example 15

To a 1000 mL round-bottom flask is added 209 g of de-ionized water, 21.9 g of glacial acetic acid and 42.4 g of silver oxide. The temperature of the solution is adjusted to 70° C. Slowly, 170 g of DMHSIPA solution (56.15% DMHSIPA in methanol) is drown into the aqueous solution. The resulting slurry is diluted with 150 g of de-ionized water, re-heated to 70° C., filtered while hot to remove insoluble silver compounds, transferred to a clean flask using 50 g of de-ionized water, re-heated to 75° C. to dissolve solids and cooled to 25° C. to induce crystallization. The product slurry is filtered on a sintered glass funnel with vacuum, washed with 40 g of DI-water (0 to 5° C.) and dried overnight in a 90° to 100° C. oven. The product analyzed as follows:

| Sample 15 - Silver Salt | |
| --- | --- |
| Weight, grams | 89.5 |
| DMSIPA, Area % LC | 98.7 |
| Monomethyl SIPA, Area % LC | 1.3 |
| Water, % KF | 0.34 |
| Sulfate, ppm as $SO_4^{2-}$, IC | <100 |
| Acetate, ppm as $AcO^{1-}$, IC | 323 |
| Strong acid, % as $H_2SO_4$ | 0 |
| Ag, x-ray fluorescence | Confirmed |
| Yield, % dry weight | 67.2 |

Example 16

To a 1000 mL round-bottom flask is added 105 g of de-ionized water and 24.4 g of cadmium(2+) acetate dihydrate. The temperature of the cadmium (2+) acetate solution is adjusted to about 24° C. Slowly, 85 g of DMHSIPA solution at ambient temperature (56.15% DMHSIPA in methanol) is drown into the aqueous solution while heating the combined solution to 50° C. The combined solution is then heated to 72° C. to dissolve solids, held for 2 minutes and cooled to 25° C. The product slurry is filtered on a sintered glass funnel with vacuum, washed with 20 g of DI-water (0 to 5° C.) and dried overnight in a 90° to 100° C. oven. The product analyzed as follows:

| Sample 16 - Cadmium (II) Salt | |
| --- | --- |
| Weight, grams | 38.0 |
| DMSIPA, Area % LC | 99.4 |
| Monomethyl SIPA, Area % LC | 0.6 |
| Water, % KF | 2.795 |
| Sulfate, ppm as $SO_4^{2-}$, IC | <100 |
| Acetate, ppm as $AcO^{1-}$, IC | 276 |
| Strong acid, % as $H_2SO_4$ | 0 |
| Cd, x-ray fluorescence | Confirmed |
| Yield, % dry weight | 66.3 |

As noted in the detailed description, metal salts made in accordance with the invention are currently used in polymer processes. The following examples illustrate the production of various polyethylene terephthalate polymers using salts made in accordance with the invention.

Example 17

To a 1000 mL round-bottom flask is added 400 g of ethylene glycol, 156 g of the sodium salt of DMHSIPA, 0.4 g of sodium bicarbonate and 0.05 g of Tetrabutyl titanate (Tyzor). The temperature is adjusted to 193° C. while distilling low boilers. The solution is held at 193° C. for 4 hours (total distillate=29.3 g). The solution is heated to 205° C. and 56 g of additional low boilers is distilled. After the addition of 24 g of ethylene glycol, the solution is cooled to 80° C., filtered and further cooled to room temperature. The product, Sodium Salt of Bis(ethylene glycol)-5-sulfoisophthalic acid (NaBis(EG)SIPA, was analyzed as follows:

| Sodium Salt of Bis(ethylene glycol)-5-sulfoisophthalic acid | |
| --- | --- |
| Weight, grams | 488.0 |
| Appearance | clear, light yellow soln. |
| Total Ester as NaBis(EG)SIPA | 37.8 |
| Acid No., mgKOH/g | 0.13 |
| Water, % KF | 0.11 |
| Sulfate, % | 0.01 |

-continued

| Sodium Salt of Bis(ethylene glycol)-5-sulfoisophthalic acid | |
|---|---|
| Absorptivity at 450 nm | 0.038 |
| Yield, % | 98.3 |

To a 450 mL stainless steel pressure reactor is added 160 g of ethylene glycol, 226.8 g of dimethylterephthalate, 0.5 g of antimony (III) oxide, 0.3 g of calcium acetate monohydrate and 27.3 g of NaBis(EG)SIPA (37.8% in ethylene glycol). The slurry is pressurized with nitrogen to 70 psig and heated to 197° C. while distilling low boilers at a pressure of 50 to 70 psig. The mixture is held at 197° C. for 2 hours. The temperature is adjusted to 220° C. while releasing pressure and is then held for 10 minutes at 220° C. The temperature is adjusted to 283° C. and is then held for 20 minutes at 283° C. The pressure is reduced to 9 mmHg while distilling the last of the low boilers. The resulting polymeric melt is poured onto aluminum foil and allowed to solidify before being ground in a mortar. The product was analyzed as follows:

| Polyethylene terephthalate polymer containing 4.4% NaBis(EG)SIPA | |
|---|---|
| Weight, grams | 234.7 |
| Appearance | Gray, opaque |
| DSC, Glass Transition temp. C. | 72.4 |
| DSC Melt Point, C. | 233.9 |
| IR-ID, PET | Match |
| Sodium, x-ray fluorescence | Confirmed |
| Yield, % dry weight | 100 |

Example 18

To a 1000 mL round-bottom flask is added 299 g of ethylene glycol, 160 g of the cesium salt of DMHSIPA (DMCsSIPA), 0.03 g of Cesium Hydroxide monohydrate and 0.02 g of Tetrabutyl titanate (Tyzor). The temperature is adjusted to 193° C. while distilling low boilers. The solution is held at 193° C. for 3.5 hours (total distillate=22.3 g). The solution is heated to 205° C. and 6.6 g of additional low boilers is distilled. After the addition of 303 g of ethylene glycol, the solution is cooled to 80° C., filtered and further cooled to room temperature. The product, Cesium Salt of Bis(ethylene glycol)-5-sulfoisophthalic acid (CsBis(EG)SIPA), was analyzed as follows:

| Cesium Salt of Bis(ethylene glycol)-5-sulfoisophthalic acid | |
|---|---|
| Weight, grams | 718.8 |
| Appearance | Slurry (white crystals) |
| Total Ester as CsBis(EG)SIPA | 27.5 |
| Acid No., mgKOH/g | 0.1 |
| Water, % KF | 0.64 |
| Sulfate, % | 0.01 |
| Absorptivity at 450 nm (in soln) | 0.06 |
| Yield, % | 107.6 |

To a 450 mL stainless steel pressure reactor is added 154 g of ethylene glycol, 226.8 g of dimethylterephthalate, 0.2 g of antimony (III) oxide, 0.3 g of calcium acetate monohydrate and 27.6 g of CsBis(EG)SIPA (27.5% in ethylene glycol). The slurry is pressurized with nitrogen to 60 psig and heated to 197° C. while distilling low boilers at a pressure of 35 to 90 psig. The mixture is held at 197° C. for 3 hours 15 minutes. The temperature is adjusted to 220° C. after releasing pressure and is then held for 10 minutes at 220° C. The temperature is adjusted to 283° C. and is then held for 20 minutes at 283° C. The pressure is reduced to 8 mmHg while distilling the last of the low boilers. The resulting polymeric melt is poured onto aluminum foil and allowed to solidify before being ground in a mortar. The product was analyzed as follows:

| Polyethylene terephthalate polymer containing 3.3% CsBis(EG)SIPA | |
|---|---|
| Weight, grams | 237.4 |
| Appearance | White, opaque |
| DSC, Glass Transition temp. C. | Not detected |
| DSC Melt Point, C. | 244.8 |
| IR-ID, PET | Match |
| Cesium, x-ray fluorescence | Confirmed |
| Yield, % dry weight | 102 |

Example 19

To a 1000 mL round-bottom flask is added 332 g of ethylene glycol, 95 g of the cadmium salt of DMHSIPA (Cd (DMSIPA)$_2$), 0.03 g of cadmium acetate dihydrate and 0.02 g of tetrabutyl titanate (Tyzor). The temperature is adjusted to 193° C. while distilling low boilers. The solution is held at 193° C. for 1.5 hours (total distillate=31 g). The solution is heated to 205° C. and 33.9 g of additional low boilers is distilled. The solution is cooled to 80° C., filtered and further cooled to room temperature. The product, cadmium (II) salt of bis(ethylene glycol)-5-sulfoisophthalic acid (Cd(Bis(EG)SIPA)$_2$), was analyzed as follows:

| Cadmium (II) Salt of Bis(ethylene glycol)-5-sulfoisophthalic acid | |
|---|---|
| Weight, grams | 356.3 |
| Appearance | Clear solution |
| Total Ester as Cd(Bis(EG)SIPA)$_2$ | 40.3 |
| Acid No., mgKOH/g | 0.87 |
| Water, % KF | 0.55 |
| Sulfate, % | <0.01 |
| Absorptivity at 450 nm (in soln) | 0.03 |
| Yield, % | 100.2 |

To a 450 mL stainless steel pressure reactor is added 154 g of ethylene glycol, 226.8 g of dimethylterephthalate, 0.2 g of antimony (III) oxide, 0.3 g of calcium acetate monohydrate and 18.9 g of Cd(Bis(EG)SIPA)$_2$ (40.3% in ethylene glycol). The slurry is pressurized with nitrogen to 60 psig and heated to 197° C. while distilling low boilers at a pressure of 40 to 90 psig. The mixture is held at 197° C. for 3 hours 15 minutes. The temperature is adjusted to 220° C. after releasing pressure and is then held for 10 minutes at 220° C. The temperature is adjusted to 283° C. and is then held for 10 minutes at 283° C. The pressure is reduced to 10 mmHg while distilling the last of the low boilers. The resulting polymeric melt is poured onto aluminum foil and allowed to solidify before being ground in a mortar. The product was analyzed as follows:

| Polyethylene terephthalate polymer containing 3.3% Cd(Bis(EG)SIPA)$_2$ | |
|---|---|
| Weight, grams | 233.4 |
| Appearance | Amber, clear |

| Polyethylene terephthalate polymer containing 3.3% Cd(Bis(EG)SIPA)₂ | |
| --- | --- |
| DSC, Glass Transition temp. C. | 44.0 (strong) |
| DSC Melt Point, C. | 242.9 (weak) |
| IR-ID, PET | Match |
| Cadmium, x-ray fluorescence | Confirmed |
| Yield, % dry weight | 100.5 |

Example 20

To a 1000 mL round-bottom flask is added 348 g of ethylene glycol, 125 g of the copper (II) salt of DMHSIPA (Cu (DMSIPA)₂), 0.03 g of copper acetate monohydrate and 0.02 g of tetrabutyl titanate (Tyzor). The temperature is adjusted to 187° C. while distilling low boilers. The solution is held at 178 to 187° C. for 33 minutes (total distillate=63.4 g). The solution is cooled to 80° C., filtered and further cooled to room temperature. The product, copper (II) salt of bis(ethylene glycol)-5-sulfoisophthalic acid (Cu(Bis(EG)SIPA)₂), was analyzed as follows:

| Copper (II) Salt of Bis(ethylene glycol)-5-sulfoisophthalic acid | |
| --- | --- |
| Weight, grams | 393.2 |
| Appearance | Clear, light blue solution |
| Total Ester as Cu(Bis(EG)SIPA)₂ | (36.5% calculated) |
| Acid No., mgKOH/g | 3.43 |
| Water, % KF | 2.18 |
| Sulfate, % | <0.01 |
| Absorptivity at 450 nm (in soln) | nr |
| Yield, % based on calculated assay | (96.1%) |

To a 450 mL stainless steel pressure reactor is added 146 g of ethylene glycol, 226.8 g of dimethylterephthalate, 0.2 g of antimony (III) oxide, 0.3 g of calcium acetate monohydrate and 26.1 g of Cu(Bis(EG)SIPA)₂ (calculated 36.5% in ethylene glycol). The slurry is pressurized with nitrogen to 60 psig and heated to 197° C. while distilling low boilers at a pressure of 40 to 70 psig. The mixture is held at 197° C. for 3 hours 15 minutes. The temperature is adjusted to 220° C. after releasing pressure and is then held for 12 minutes at 220° C. The temperature is adjusted to 283° C. and is then held for 20 minutes at 283° C. The pressure is reduced to 10 mmHg while distilling the last of the low boilers. The resulting polymeric melt is poured onto aluminum foil and allowed to solidify before being ground in a mortar. The product was analyzed as follows:

| Polyethylene terephthalate polymer containing 4% Cu(Bis(EG)SIPA)₂ | |
| --- | --- |
| Weight, grams | 235.9 |
| Appearance | Black, glassy |
| DSC, Glass Transition temp. C. | 39.8 |
| DSC Melt Point, C. | 189.8 |
| IR-ID, PET | Match |
| Copper, x-ray fluorescence | Confirmed |
| Yield, % dry weight | 100.8 |

Example 21

To a 1000 mL round-bottom flask is added 401 g of ethylene glycol, 147.73 g of the cobalt salt of DMHSIPA (Co (DMSIPA)₂), 0.03 g of cobalt acetate tetrahydrate and 0.02 g of tetrabutyl titanate (Tyzor). The temperature is adjusted to 193° C. while distilling low boilers. The solution is held at 193 C for 3.5 hours (total distillate=60 g). The solution is heated to 205° C. and 34.5 g of additional low boilers is distilled. After the addition of 81 g of ethylene glycol, the solution is cooled to 80° C., filtered and further cooled to room temperature. The product, cobalt (II) salt of bis(ethylene glycol)-5-sulfoisophthalic acid was analyzed as follows:

| Cobalt (II) Salt of Bis(ethylene glycol)-5-sulfoisophthalic acid | |
| --- | --- |
| Weight, grams | 536.6 |
| Appearance | Dark purple solution |
| Total Ester as Co(Bis(EG)SIPA)₂ | (32.3% calculated) |
| Acid No., mgKOH/g | 1.84 |
| Water, % KF | 1.27 |
| Sulfate, % | <0.01 |
| Absorptivity at 450 nm (in soln) | Nr |
| Yield, % based on calculated assay | (97.9%) |

To a 450 mL stainless steel pressure reactor is added 158 g of ethylene glycol, 226.8 g of dimethylterephthalate, 0.2 g of antimony (III) oxide, 0.3 g of calcium acetate monohydrate and 23.5 g of Co(Bis(EG)SIPA)₂ (calculated 32.3% in ethylene glycol). The slurry is pressurized with nitrogen to 60 psig and heated to 197° C. while distilling low boilers at a pressure of 40 to 160 psig. The mixture is held at 197° C. for 180 minutes. The temperature is adjusted to 220° C. after releasing pressure and is then held for 10 minutes at 220° C. The temperature is adjusted to 283° C. and is then held for 10 minutes at 283° C. The pressure is reduced to 11 mmHg while distilling the last of the low boilers. The resulting polymeric melt is poured onto aluminum foil and allowed to solidify before being ground in a mortar. The product was analyzed as follows:

| Polyethylene terephthalate polymer containing 3.3% Co(Bis(EG)SIPA)₂ | |
| --- | --- |
| Weight, grams | 228.4 |
| Appearance | Dark Amber, clear |
| DSC, Glass Transition temp. C. | 59.3 (strong) |
| DSC Melt Point, C. | 199.8 (weak) |
| IR-ID, PET | Match |
| Cobalt, x-ray fluorescence | Confirmed |
| Yield, % dry weight | 97.6 |

The following paragraphs illustrate the manufacture of polyamides modified with salts manufactured in accordance with the invention.

Example 22

This example illustrates the production of a polyamide 6/10 salt that is utilized in the following examples. To a 2000 mL round-bottom flask is added 1175 g of n-butanol and 255 g of sebasic acid. The slurry is heated to 61 to 63° C. and held for 30 minutes to dissolve the sebasic acid. Molten 1,6-Hexamethylene diamine (155.1 g) is slowly added while allowing the temperature to drift upward. The resulting slurry is heated to reflux, cooled to 25° C. and filtered. The wet cake is reslurried in excess acetone, re-filtered and dried in a 70° C. vacuum oven to provide 391.4 g of white solid. This product (polyamide 6/10 salt) was analyzed as follows:

| Polyamide 6/10 Salt | |
|---|---|
| Weight, grams | 391.4 |
| DSC, Melt Point at 5 C./min ramp, C. | 178.2 |
| Yield, % dry weight | 97.6 |

Example 23

To a 1000 mL round bottom flask fitted with a Dean-Stark trap is added 400 g of para-diisopropylbenzene, 127 g of polyamide 6/10 salt (HMDA-Sebasic acid salt), 1 g of sebasic acid and 2.4 g of the sodium salt of dimethyl-5-sulfoisophthalic acid. The slurry is heated to 208° C. while removing water of reaction in the Dean-Stark trap. The slurry becomes a two-phase liquid-liquid system at around 181° C. followed by the solidification of the lower layer as the water of reaction is removed during the heat-up to 208° C. A total of 12.9 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% NaDMSIPA | |
|---|---|
| Weight, grams | 107.6 |
| Appearance | tan |
| DSC, Melt Point at 20 C./min ramp, C. (initial pass) | 223.6 |
| DSC, Melt Point at 20 C./min ramp, C. (final pass) | 220.0 |
| IR-ID, Polyamide | Match |
| Sodium, ICP | Confirmed |
| Yield, % dry weight | 92.8 |

Example 24

To a 1000 mL round bottom flask fitted with a Dean-Stark trap is added 400 g of meta-diisopropylbenzene, 127 g of polyamide 6/10 salt (HMDA-Sebasic acid salt), 1 g of sebasic acid and 2.4 g of cesium salt of dimethyl-5-sulfoisophthalic acid. The slurry is heated to 203° C. while removing water of reaction in the Dean-Stark trap. The slurry becomes a two-phase liquid-liquid system followed by the solidification of the lower layer as the water of reaction is removed during the heat-up to 203° C. A total of 10.0 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% CsDMSIPA | |
|---|---|
| Weight, grams | 115.4 |
| Appearance | tan |
| DSC, Melt Point at 20 C./min ramp, C. (initial pass) | 223.1 |
| DSC, Melt Point at 20 C./min ramp, C. (final pass) | 221.6 |
| IR-ID, Polyamide | Match |
| Cesium, x-ray fluorescence | Confirmed |
| Yield, % dry weight | 99.4 |

Example 25

To a 1000 mL round bottom flask fitted with a Dean-Stark trap is added 400 g of meta-diisopropylbenzene, 127 g of polyamide 6/10 salt (HMDA-Sebasic acid salt), 1 g of sebasic acid and 2.4 g of the silver (I) salt of dimethyl-5-sulfoisophthalic acid. The slurry is heated to 200° C. while removing water of reaction in the Dean-Stark trap. The slurry becomes a two-phase liquid-liquid system followed by the solidification of the lower layer as the water of reaction is removed during the heat-up to 200° C. A total of 12.4 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% AgDMSIPA | |
|---|---|
| Weight, grams | 114.0 |
| Appearance | black |
| DSC, Melt Point at 20 C./min ramp, C. (initial pass) | 221.6 |
| DSC, Melt Point at 20 C./min ramp, C. (final pass) | 218.4 |
| IR-ID, Polyamide | Match |
| Silver, x-ray fluorescence | Confirmed |
| Yield, % dry weight | 98.3 |

Example 26

To a 1000 mL round bottom flask fitted with a Dean-Stark trap is added 400 g of para-diisopropylbenzene, 127 g of polyamide 6/10 salt (HMDA-Sebasic acid salt), 1 g of sebasic acid and 2.4 g of copper (II) salt of dimethyl-5-sulfoisophthalic acid. The slurry is heated to 209° C. while removing water of reaction in the Dean-Stark trap. The slurry becomes a two-phase liquid-liquid system at around 165° C. followed by the solidification of the lower layer as the water of reaction is removed during the heat-up to 209° C. A total of 13.3 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% Cu(DMSIPA)$_2$ | |
|---|---|
| Weight, grams | 114.3 |
| Appearance | Dark gray |
| DSC, Melt Point at 20 C./min ramp, C. (Initial pass) | (216.6, 221.7, 232.4) |
| DSC, Melt Point at 20 C./min ramp, C. (final pass) | 218.5 |
| IR-ID, Polyamide | Match |
| Copper, x-ray fluorescence | Confirmed |
| Yield, % dry weight | 98.5 |

Example 27

To a 1000 mL round bottom flask fitted with a Dean-Stark trap is added 400 g of tri-isopropylbenzene, 127 g of polyamide 6/10 salt (HMDA-Sebasic acid salt), 1 g of sebasic acid and 2.4 g of cobalt (II) salt of dimethyl-5-sulfoisophthalic acid. The slurry is heated to 230° C. while removing water of reaction in the Dean-Stark trap. The slurry becomes a two-phase liquid-liquid system at around 169° C. followed by the solidification of the lower layer as the water of reaction is removed during the heat-up to 230 C. A total of 12.7 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% Co(DMSIPA)$_2$ | |
|---|---|
| Weight, grams | 114.1 |
| Appearance | Light purple |
| DSC, Melt Point at 20 C./min ramp, C. (initial pass) | 226.8 |
| DSC, Melt Point at 20 C./min ramp, C. (final pass) | 220.7 |
| IR-ID, Polyamide | Match |
| Cobalt, x-ray fluorescence | Confirmed |
| Yield, % dry weight | 98.4 |

Example 28

To a 1000 mL round bottom flask fitted with a Dean-Stark trap is added 400 g of tri-isopropylbenzene, 127 g of polyamide 6/10 salt (HMDA-Sebasic acid salt), 1 g of sebasic acid and 2.4 g of cadmium (II) salt of dimethyl-5-sulfoisophthalic acid. The slurry is heated to 238° C. while removing water of reaction in the Dean-Stark trap. The slurry becomes a two-phase liquid-liquid system at around 170° C. followed by the solidification of the lower layer as the water of reaction is removed during the heat-up to 238° C. A total of 10 g of water was distilled to the receiver. The slurry is cooled to 50 to 60° C. and the solvent poured off of the solid. Methanol (200 g) is added to the solid and the resulting slurry refluxed for one hour. The product was filtered on a sintered glass funnel and dried overnight in a 70° C. vacuum oven. The product was ground and analyzed as follows:

| Polyamide 6/10 polymer containing 2% Cd(DMSIPA)$_2$ | |
|---|---|
| Weight, grams | 122.8 |
| Appearance | Light tan |
| DSC, Melt Point at 20 C./min ramp, C. (initial pass) | 225.0 |
| DSC, Melt Point at 20 C./min ramp, C. (final pass) | 220.0 |
| IR-ID, Polyamide | Match |
| Cadmium, x-ray fluorescence | Confirmed |
| Yield, % dry weight | 105.9 |

While the invention is described with respect to various embodiments thereof, it will be understood by those skilled in the art that various changes in detail may be made therein without departing from the spirit, scope, and teaching of the invention. Accordingly, the invention herein disclosed is to be limited only as specified in the claims.

That which is claimed is:

1. A method of preparing a metal salt of a dialkyl ester of 5-sulfoisophthalic acid, the method comprising the steps of:
   contacting a dialkyl ester of 5-sulfoisophthalic acid with a metal cation in an aqueous buffered reaction mixture to form the metal salt of said metal cation and said dialkyl ester, wherein said aqueous buffered reaction mixture is buffered by the acetate of said metal cation; and
   recovering the salt product from the reaction mixture.

2. A method according to claim 1 wherein the step of contacting a dialkyl ester with a metal cation comprises reacting 5-sulfoisophthalic acid with an alcohol under conditions sufficient to form a solution containing a dialkyl ester of 5-sulfoisophthalic acid followed by drowning said solution of dialkyl ester into a solution buffered by the acetate of said metal cation thereby forming said buffered reaction mixture.

3. A method according to claim 1 wherein the step of contacting comprises the steps of:
   forming an aqueous buffered reaction mixture comprising 5-sulfoisophthalic acid, an alcohol, and a metal cation;
   maintaining said aqueous buffered reaction mixture under conditions sufficient to form the metal salt of a dialkyl ester of 5-sulfoisophthalic acid.

4. A method according to claim 1 wherein the aqueous buffered solution is formed at least in part by the in situ combination of acetic acid and aqueous metal hydroxide.

5. A method according to claim 1 further comprising the steps of:
   cooling the reaction mixture to a temperature sufficient to induce crystallization of said metal salt; and
   separating the metal salt.

6. A method according to claim 5 wherein the reaction mixture is heated to a temperature sufficient to dissolve substantially all of the solids contained within the reaction mixture prior to the step of cooling the reaction mixture to induce crystallization.

7. A method according to claim 1 wherein the quantity of said acetate in said reaction mixture is sufficient to buffer the reaction mixture so as to avoid hydrolysis of ester groups.

8. A method according to claim 1 wherein the dialkyl ester of 5-sulfoisophthalic acid is dimethyl-5-sulfoisophthalic acid.

9. A method according to claim 1 wherein said metal is selected from the group consisting of sodium, potassium, lithium, rubidium, cesium, magnesium, calcium, strontium, barium, manganese, iron (II), cobalt, nickel, copper (II), zinc, silver (I), and cadmium.

10. A method according to claim 5 further comprising combining the metal salt with a polymer.

* * * * *